United States Patent [19]

Saripalli et al.

[11] Patent Number: 5,431,342
[45] Date of Patent: Jul. 11, 1995

[54] NOZZLE PROVIDING A LAMINAR EXHAUST STREAM

[75] Inventors: Kondala R. Saripalli, St. Louis; Eugene A. Myers, St. Charles; Richard D. Lawson, Overland, all of Mo.

[73] Assignee: McDonnell Douglas Corporation, Huntington Beach, Calif.

[21] Appl. No.: 164,662

[22] Filed: Dec. 8, 1993

Related U.S. Application Data

[63] Continuation of Ser. No. 980,344, Nov. 23, 1992, abandoned.

[51] Int. Cl.$^6$ ............................................. B05B 17/06
[52] U.S. Cl. ..................... 239/102.2; 239/590.3; 239/589
[58] Field of Search ................ 239/102.2, 589, 590.3, 239/601, 596, 602, 590.5, DIG. 1

[56] References Cited

U.S. PATENT DOCUMENTS

| | | |
|---|---|---|
| 1,840,863 | 1/1932 | Wenderhold . |
| 1,967,577 | 7/1934 | Katz ................... 239/589 X |
| 2,453,595 | 11/1948 | Rosenthal . |
| 2,574,003 | 11/1951 | Wymer . |
| 3,473,562 | 10/1969 | Ellison ................... 239/590.3 |
| 3,679,132 | 7/1972 | Vehe et al. ............ 239/102.2 X |
| 4,004,736 | 1/1977 | George ................... 239/102.2 |
| 4,034,025 | 7/1977 | Martner ................. 239/102.2 X |
| 4,251,031 | 2/1981 | Martin et al. ........... 239/102.2 X |
| 4,393,991 | 7/1983 | Jeffras et al. ........... 239/102.2 |
| 4,546,920 | 10/1985 | Torgerson ............... 239/102.2 |
| 4,646,967 | 3/1987 | Geitham ................. 239/4 |
| 4,647,013 | 3/1987 | Giachino et al. ......... 251/331 |
| 4,690,326 | 9/1987 | Gill ...................... 239/223 |
| 4,930,701 | 6/1990 | Porter et al. ........... 239/102.2 |

FOREIGN PATENT DOCUMENTS 144826 6/1962 U.S.S.R. .

Primary Examiner—Andres Kashnikow
Assistant Examiner—Lesley D. Morris
Attorney, Agent, or Firm—James M. Skorich; John P. Scholl

[57] ABSTRACT

A nozzle is adapted to receive an ultrasonic transducer. The nozzle includes a cylindrical plenum chamber. An annular passageway circumscribes the plenum chamber. A porous material forms the annular walls of the plenum chamber and separates the plenum chamber from the passageway. The plenum chamber fluidly communicates with the passageway through the porous material. The passageway fluidly communicates with a supply line that, in turn, fluidly communicates with a pump that supplies water. The plenum chamber has a circular exhaust orifice for the exhaust of water from the nozzle. The plenum chamber contains an unobstructed forming space to facilitate the forming of ultrasonic waves. The diameter of the plenum chamber divided by the diameter of the exhaust orifice is a quotient of at least three. The periphery of the exhaust orifice is an edge formed by the intersection of two concentric surfaces of revolution, each of which is symmetrical about the centerline of the plenum chamber and lies at a respective angle with respect to the centerline.

34 Claims, 3 Drawing Sheets

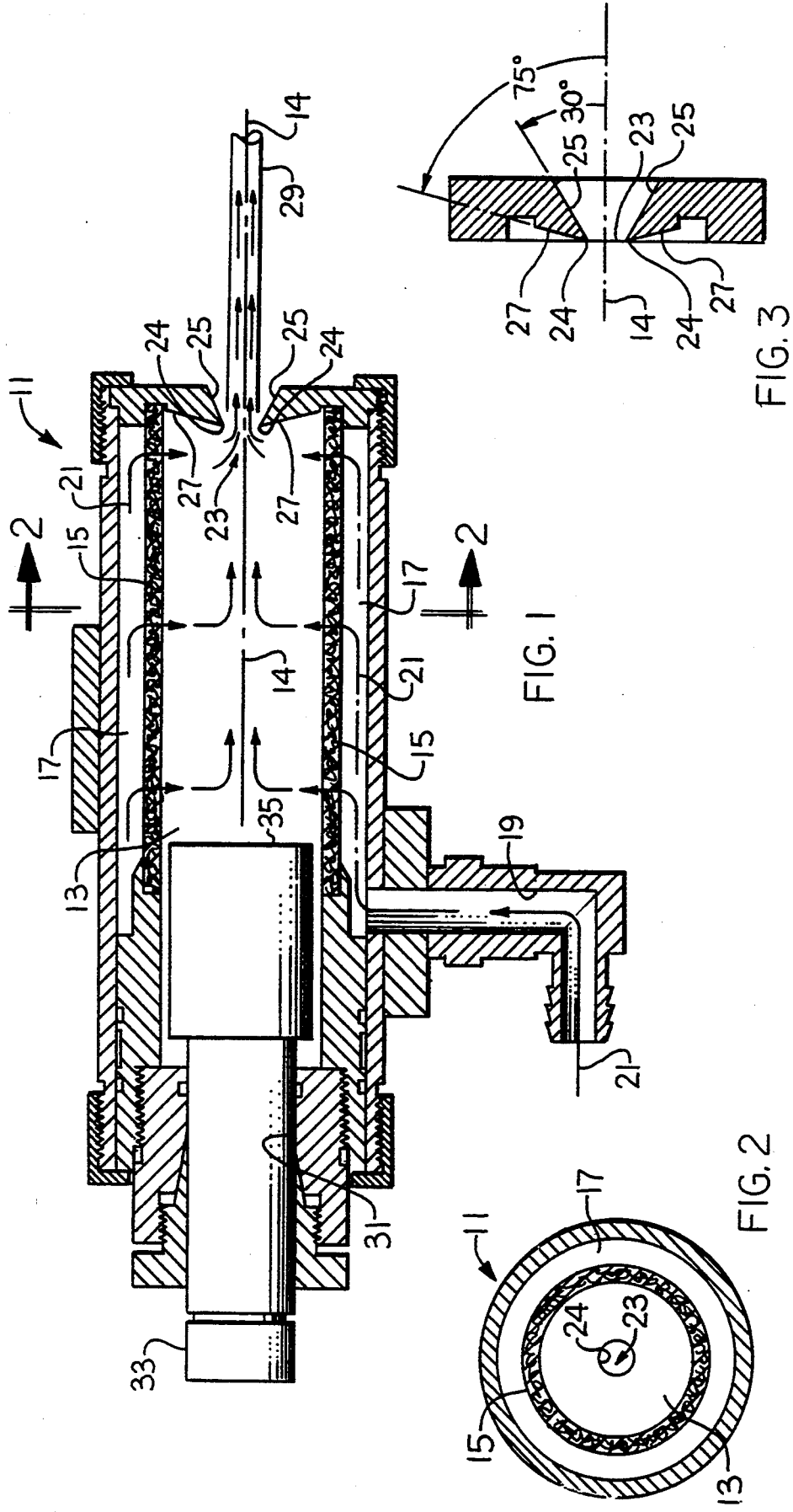

NOZZLE PROVIDING A LAMINAR EXHAUST STREAM

This is a continuation of application Ser. No. 07/980,344 filed on 23 Nov. 1992, and now abandoned.

BACKGROUND OF THE INVENTION

1. Field of the Invention

The present invention relates to nozzles and, more particularly, to a nozzle including a circular exhaust orifice having a periphery composed of an edge formed by the intersection of two concentric surfaces of revolution.

2. Description of the Prior

The use of ultrasonic waves to nondestructively inspect composite laminate parts for porosity, delaminations, defects in bonding, and the presence of foreign objects, is well known. Testing with ultrasonic waves requires that a coupling medium, typically water, be used to conduct the ultrasonic waves between the transducer and the test object. Early apparatus required submersion of the test object, while more recent devices use a nozzle to produce a column of water that extends between the transducer and the test object and contains the ultrasonic waves.

Current ultrasonic testing devices are of two types, pulse echo and through transmission. Pulse echo devices measure the difference in time between the transmitted waves and the waves respectively reflected by the test piece, while through transmission apparatus measure the attenuation of the transmitted waves after they pass through the test piece. The former apparatus require one column of water between the emitting transducer and the test piece, while the latter additionally require a second column of water to couple the test piece with a receiving transducer.

When the flow in the column of water becomes nonlaminar, the column breaks up and the internal reflection of the ultrasonic waves contained in the column becomes scattered rather than remaining focused. Nonlaminar flow also causes an increase in the number of droplets reflecting off the test part and impinging onto the column to cause turbulence. For the foregoing reasons, the signal to noise ratio of the ultrasonic waves being transmitted in the column of water decreases as the flow becomes nonlaminar.

The distance between the nozzle and the test piece is known as the throw distance. Ultrasonic testing devices using the nozzles of the prior art avoid the onset of an unacceptable signal to noise ratio by keeping the throw distance less than that which would lead to nonlaminar flow and, concomitantly, an unacceptable signal to noise ratio. With the nozzles of the prior art, the maximum throw distance when the column of water is horizontal is typically two to three inches.

In a number of newer structures, protrusions such as flanges, fibs, co-cured stiffeners and other structural supports oftentimes prevent using the nozzle within this limited throw distance. The ever increasing presence of these protrusions coupled with the inherent limitations of the prior art nozzles restricts the beneficial use of the automated ultrasonic scanning devices that have been developed.

The transition to nonlaminar flow in the water column exhausted by a nozzle is also a function of flow rate, with the throw distance at which nonlaminar flow occurs decreasing as the flow rate increases. The flow rate must be low enough to prevent nonlaminar flow from occurring within the throw distance over which the nozzle is intended to provide an acceptable signal to noise ratio. However, the prior art nozzles typically require a flow rate that is so low that the column of water droops due to gravity when the column is horizontal.

Among other problems, droop causes a difference between the location actually being inspected and the inspection location on the test piece calculated by the computer program used by the automated ultrasonic scanning device. This error occurs because the software cannot accurately compensate for droop, especially when the contour of the surface of the test piece rapidly changes.

SUMMARY OF THE INVENTION

Briefly, the invention is a nozzle that includes a cylindrical plenum chamber. The annular walls of the plenum chamber are porous. Water enters the plenum chamber radially through the porous walls. Once inside the plenum chamber, the direction of fluid flow changes from radial to axial. A circular exhaust orifice at one end of the plenum chamber provides for the exhaust of water from the plenum chamber.

The periphery of the exhaust orifice is an edge formed by the intersection of two concentric surfaces of revolution. Both surfaces of revolution are symmetrical about the axial centerline of the plenum chamber, and each surface lies at a respective angle to the centerline. The ratio of the diameter of the plenum chamber divided by the diameter of the exhaust orifice is a quotient of at least three.

An ultrasonic transducer is inserted in one end of the nozzle. The transducer emits ultrasonic energy. Ultrasonic waves are formed in an unobstructed forming space extending between the transducer and the exhaust orifice. The ultrasonic waves are used to nondestructively test various structures. The exhausted water forms a column that transmits the ultrasonic waves between the nozzle and the structure being tested.

Contrasting the invented nozzle and comparable nozzles of the prior art, the laminar flow of the horizontal column of water exhausted by the invented nozzle provides for an acceptable signal to noise ratio for the ultrasonic waves being transmitted therein over a throw distance at least five times that of prior art nozzles. The invented nozzle thereby allows automated ultrasonic scanning devices to inspect structures having protrusions and complex shapes.

Furthermore, the invented nozzle produces a column of water that retains its laminar flow characteristics over the aforementioned increased throw distance even at a flow rate significantly above the maximum flow rate usable by prior art nozzles. The invented nozzle thus reduces column droop, in turn reducing or eliminating any inaccuracy occasioned by the horizontal column of water impinging on a point on a test piece different from that calculated by an automated ultrasonic scanning device.

BRIEF DESCRIPTION OF THE DRAWINGS

FIG. 1 is a longitudinal cross section of an embodiment of the invented nozzle.

FIG. 2 is a sectional view of the described embodiment of the invented nozzle taken along line 2—2 of FIG. 1.

FIG. 3 is an enlarged sectional view of the end of the described embodiment of the invented nozzle containing the exhaust orifice.

DETAILED DESCRIPTION OF AN EMBODIMENT OF THE INVENTION

Figure 4:
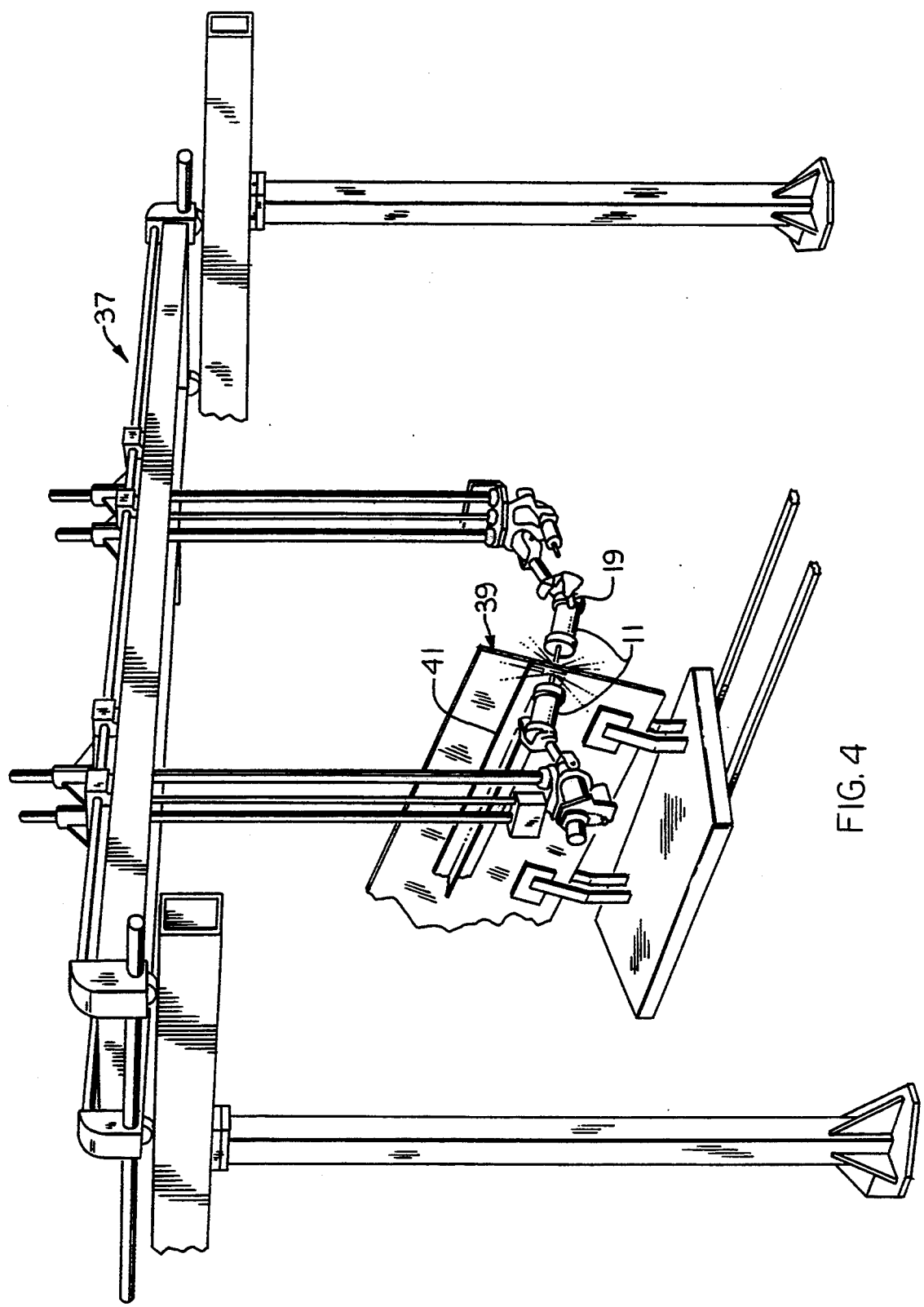
FIG. 4 is a perspective view showing the described embodiment of the invented nozzle as part of an automated ultrasonic scanning apparatus inspecting a test piece.

Turning to the drawings, nozzle 11 is an embodiment of the invention. FIG. 1 shows a longitudinal cross section of nozzle 11, and FIG. 2 is a sectional view of nozzle 11 taken along line 2—2 of FIG. 1. Cylindrical plenum chamber 13 is contained within nozzle 11. Plenum chamber 13 has axial centerline 14.

Porous material 15 is annular in shape, laterally circumscribing plenum chamber 13 and forming its diameter. Passageway 17 is also annular and circumscribes porous material 15. Porous material 15 thus separates plenum chamber 13 and passageway 17, but allows fluid communication between them through its pores. Supply line 19 fluidly communicates with passageway 17. Water 21 Is pumped from a source (not shown) into supply line 19.

Circular exhaust orifice 23 is located in an end of nozzle 11. The center of exhaust orifice 23 lies on centerline 14. The periphery of exhaust orifice 23 is edge 24 formed by the intersection of concentric surfaces of revolution 25 and 27. Surfaces 25 and 27 are both symmetrical about centerline 14. As indicated in FIG. 3, surface 25 lies at an angle of 30° to centerline 14, and surface 27 lies at an angle of 75° to centerline 14. When the total pressure in plenum chamber 13 is at its operating level, plenum 13 exhausts water 21 through exhaust orifice 23 in the form of cylindrical water column 29.

Transducer opening 31 is located in the end of nozzle 11 lying opposite the end containing exhaust orifice 23. Ultrasonic transducer 33 is threadably inserted into transducer opening 31. Emitting surface 35 of ultrasonic transducer 33 is planar and circular. Emitting surface 35 emits ultrasonic energy. The center of emitting surface 35 lies on centerline 14. Forming space 37 is cylindrical, has a diameter equal to the diameter of plenum chamber 13, and extends longitudinally between emitting surface 35 and exhaust orifice 23. There is no structure of nozzle 11 projecting into forming space 37. Forming space 37 facilitates the formation of ultrasonic waves from the ultrasonic energy emitted from emitting surface 35.

The total pressure of water 21 in plenum chamber 13 is composed of the sum of the dynamic pressure and the static pressure therein. Porous material 15 restricts the flow of water 21 in passageway 17 so that only its radial velocity component affects the water located in plenum chamber 13. In this manner, porous material 15 virtually eliminates the effects of the axial velocity component and turbulence of the flow in passageway 17. Thus, while permitting the static pressure in plenum chamber 13 to be maintained, porous material 15 minimizes the dynamic pressure therein. This minimizes turbulence in water column 29.

The dynamic pressure in plenum chamber 13, and hence the turbulence in water column 29, are also minimized by keeping the ratio of the diameter of plenum chamber 13 divided by the diameter of exhaust orifice 23 at a quotient of at least three.

Edge 24 prevents a boundary layer from forming in water column 29. As the presence of a boundary layer precipitates the onset of nonlaminar flow in such a column of water, preventing its formation has the salutary effect of delaying the onset of nonlaminar flow in water column 29.

The 30° angle between surface 25 and centerline 14 prevents the Coanda effect from causing water 21 being exhausted from exhaust orifice 23 from adhering to surface 25 and forming a conic shape rather than the preferred cylinder of water column 29. Other embodiments of the invention may use a different angle as long as it is at least 30°.

The 75° angle between surface 27 and centerline 14 prevents surface 27 from reflecting the ultrasonic waves back onto emitting surface 35, from where the waves subsequently could be reflected through exhaust orifice 23, into water column 29, and through or off the test piece. Such reflected ultrasonic waves are spurious and degrade the signal to noise ratio of the ultrasonic waves providing valid test data. The angled surface 27 instead reflects ultrasonic waves that are not contained in water column 29 into the walls of plenum chamber 13, where they decay. Other embodiments of the invention may use a different angle for the foregoing surface of revolution as long as it is no greater than 75°.

The cumulative effect of the improvements set out herein is to create and maintain laminar flow in water column 29 over a throw distance many times that of comparable prior art nozzles. This condition keeps the ultrasonic waves being transmitted by water column 29 unobstructed and focused within water column 29, rather than reflected and scattered by the break up of a water column caused by nonlaminar flow.

When column 29 is near horizontal, the laminar flow therein also causes less spray when column 29 impinges the test piece. This results in fewer water droplets being reflected back into water column 29. As the impinging water droplets create spurious signals that degrade the signal to noise ratio, the reduction of noise from this source further improves the signal to noise ratio over that obtainable using the nozzles of the prior art.

Due to the improved focus of the ultrasonic waves within water column 29 and the reduced noise from droplets impinging on water column 29, nozzle 11 provides an acceptable signal to noise ratio over a throw distance at least five times that of comparable prior art nozzles when the respective water columns are horizontal. Furthermore, nozzle 11 can obtain the aforementioned throw distance while using a flow rate appreciably higher than the flow rates of comparable art nozzles. This higher flow rate minimizes the droop of water column 29 caused by gravity when water column 29 is horizontal.

The significantly greater throw distance together with the minimized droop realized by the invented nozzle enables the nozzle to be located further away from the test piece than would otherwise be the case. This allows automated ultrasonic scanning devices to use the nozzle and ultrasonic transducer contained therein to nondestructively test structures having complex contours and having flanges, ribs, co-cured stiffeners and other structural supports projecting from the surface of the test piece.

By way of example, for plenum chamber 13 having a diameter of 2.125 inches, exhaust orifice 23 having a diameter of 0.187 inches and a flow rate therethrough of 3 gallons per minute, and water column 29 lying horizontal, the signal to noise ratio was acceptable for a throw distance of at least 10 inches. In comparison, a nozzle of the prior art having the same dimensions, exhaust flow rate, and a horizontal water column had an acceptable signal to noise ratio for a throw distance of only approximately 2 inches. Moreover, the signal to noise ratio remained acceptable for nozzle 11 even when its flow rate was increased to virtually eliminate droop over the 10 inch throw distance.

FIG. 4 shows nozzle 11 attached to automated ultrasonic scanning device 37. Test piece 39 is being ultrasonically inspected.

Figure 5:
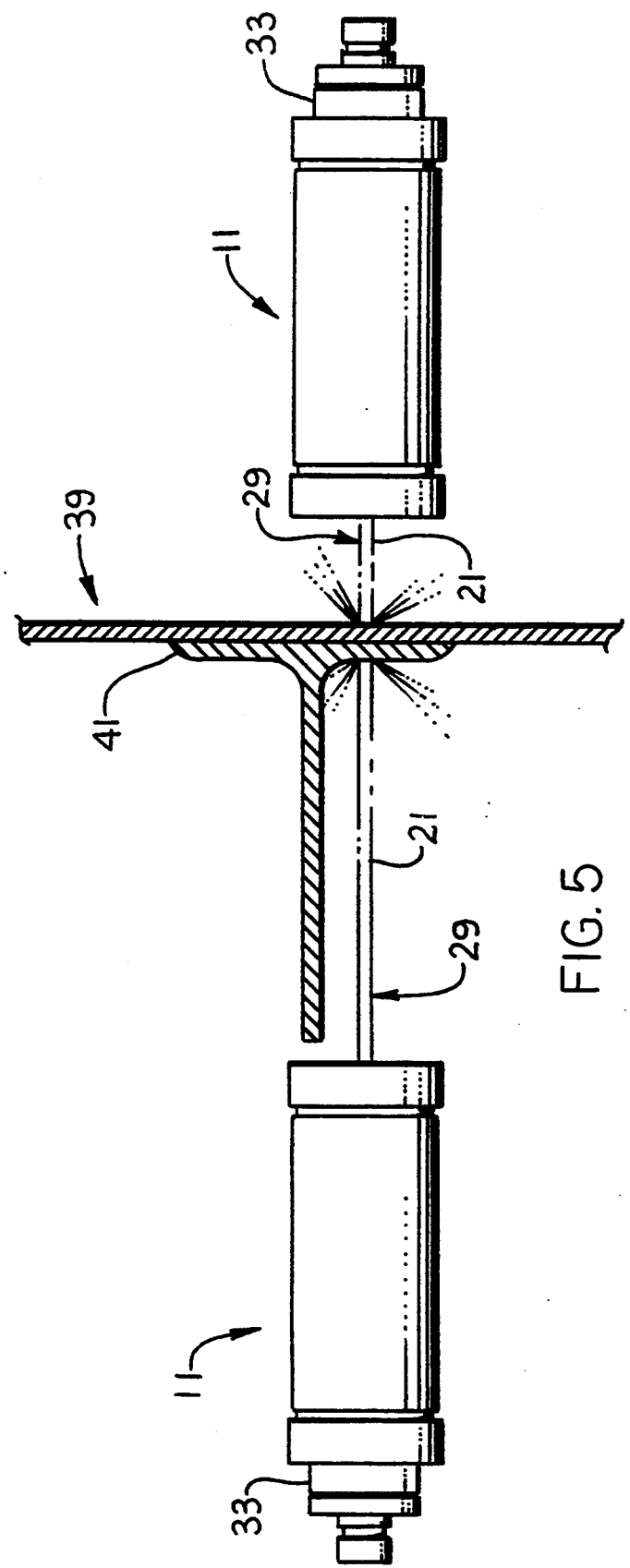
FIG. 5 shows the described embodiment of the invented nozzle inspecting a section of the test piece that has a protruding flange.

FIG. 5 shows nozzle 11 testing an area of test piece 39 having protruding flange 41. This figure shows how the greater throw distance of nozzle 11 can be used to advantage in testing items having such protruding structures.

Changes and modifications to the specifically described embodiment may be made without departing from the scope of the invention, as the invention is intended to be limited only by the scope of the appended claims.

What is claimed is:

1. A nozzle for providing a laminar exhaust stream comprising:
   a cylindrical plenum chamber having an exhaust orifice;
   an annular passageway laterally circumscribing said plenum chamber and having a longitudinal wall in common with said plenum chamber; and
   said wall being porous, whereby
   said passageway and said plenum chamber fluidly communicate in a radial direction.

2. The nozzle recited in claim 1 wherein said exhaust orifice has an annular edge projecting into said plenum chamber.

3. The nozzle recited in claim 2 further comprising energy means for generating ultrasonic energy.

4. The nozzle recited in claim 3 wherein:
   said energy means includes a substantially planar emitting surface for emitting ultrasonic energy;
   said emitting surface is approximately circular, has a diameter, and faces said exhaust orifice;
   said plenum chamber contains a forming space for the formation of ultrasonic waves; and
   said forming space is cylindrical, has a diameter no less than the diameter of said emitting surface, extends longitudinally from said emitting surface to said exhaust orifice, and is substantially unobstructed by structure, whereby
   the ultrasonic waves can form in said forming space without interference by structure.

5. The nozzle recited in claim 4 wherein:
   said exhaust orifice includes inner surface means for preventing the exhaust stream from being affected by the Coanda effect;
   said exhaust orifice passes through an end of said plenum chamber; and
   said end of said plenum chamber includes outer surface means for reflecting ultrasonic waves towards said wall.

6. The nozzle recited in claim 5 wherein fluid communication between said passageway and said exhaust orifice is provided solely through said wall.

7. The nozzle recited in claim 4 wherein fluid communication between said passageway and said exhaust orifice is provided solely through said wall.

8. The nozzle recited in claim 4 wherein:
   said annular edge is formed by the intersection of an outer surface of revolution and an inner surface of revolution;
   an end of said plenum chamber includes said outer surface of revolution;
   said plenum chamber has an axial centerline that is centrally located in each transverse cross section of said plenum chamber;
   said inner and outer surfaces of revolution are symmetrical about said centerline;
   an inner angle of at least 30° is included between said centerline and said inner surface of revolution; and
   an outer angle no greater than 75° is included between said centerline and said outer surface of revolution.

9. The nozzle recited in claim 2 wherein:
   said annular edge is formed by the intersection of an outer surface of revolution and an inner surface of revolution;
   an end of said plenum chamber includes said outer surface of revolution;
   said plenum chamber has an axial centerline that is centrally located in each transverse cross section of said plenum chamber;
   said inner and outer surfaces of revolution are symmetrical about said centerline;
   an inner angle of at least 30° is included between said centerline and said inner surface of revolution; and
   an outer angle no greater than 75° is included between said centerline and said outer surface of revolution.

10. The nozzle recited in claim 9 further comprising energy means for generating ultrasonic energy.

11. The nozzle recited in claim 10 wherein:
    said energy means includes a substantially planar emitting surface for emitting ultrasonic energy;
    said emitting surface is approximately circular, has a diameter, and faces said exhaust orifice;
    said plenum chamber contains a forming space for the formation of ultrasonic waves; and
    said forming space is cylindrical, has a diameter no less than the diameter of said emitting surface, extends longitudinally from said emitting surface to said exhaust orifice, and is substantially unobstructed by structure, whereby
    the ultrasonic waves can form in said forming space without interference by structure.

12. The nozzle recited in claim 9 wherein said end of said plenum chamber consists of said outer surface of revolution and said exhaust orifice passing therethrough.

13. The nozzle recited in claim 9 wherein fluid communication between said passageway and said exhaust orifice is provided solely through said wall.

14. The nozzle recited in claim 2 wherein fluid communication between said passageway and said exhaust orifice is provided solely through said wall.

15. The nozzle recited in claim 2 wherein:
    said exhaust orifice includes inner surface means for preventing the exhaust stream from being affected by the Coanda effect;
    said exhaust orifice passes through an end of said plenum chamber; and said end of said plenum chamber includes outer surface means for reflecting ultrasonic waves towards said wall.

16. The nozzle recited in claim 1 further comprising energy means for generating ultrasonic energy.

17. The nozzle recited in claim 16 wherein:
said energy means includes a substantially planar emitting surface for emitting ultrasonic energy;
said emitting surface is approximately circular, has a diameter, and faces said exhaust orifice;
said plenum chamber contains a forming space for the formation of ultrasonic waves; and
said forming space is cylindrical, has a diameter no less than the diameter of said emitting surface, extends longitudinally from said emitting surface to said exhaust orifice, and is substantially unobstructed by structure, whereby
the ultrasonic waves can form in said forming space without interference by structure.

18. The nozzle recited in claim 17 wherein fluid communication between said passageway and said exhaust orifice is provided solely through said wall.

19. The nozzle recited in claim 1 wherein:
said plenum chamber has a plenum chamber diameter;
said exhaust orifice has an orifice diameter; and
said plenum chamber diameter divided by said orifice diameter has a quotient of at least three.

20. The nozzle recited in claim 19 wherein said exhaust orifice has an annular edge projecting into said plenum chamber.

21. The nozzle recited in claim 20 wherein:
said annular edge is formed by the intersection of an outer surface of revolution and an inner surface of revolution;
an end of said plenum chamber has an axial centerline that is centrally located in each transverse cross section of said plenum chamber;
said inner and outer surfaces of revolution are symmetrical about said centerline;
an inner angle of at least 30° is included between said centerline and said inner surface of revolution; and
an outer angle no greater than 75° is included between said centerline and said outer surface of revolution.

22. The nozzle recited in claim 20 wherein:
the energy means includes a substantially planar emitting surface for emitting ultrasonic energy;
said emitting surface is approximately circular, has a diameter, and faces said exhaust orifice;
said plenum chamber contains a forming space for the formation of ultrasonic waves; and
said forming space is cylindrical, has a diameter no less than the diameter of said emitting surface, extends longitudinally from said emitting surface to said exhaust orifice, and is substantially unobstructed by structure, whereby
the ultrasonic waves can form in said forming space without interference by structure.

23. The nozzle recited in claim 19 further comprising:
energy means for generating ultrasonic energy, wherein;
said energy means includes a substantially planar emitting surface for emitting ultrasonic energy;
said emitting surface is approximately circular, has a diameter, and faces said exhaust orifice;
said plenum chamber contains a forming space for the formation of ultrasonic waves; and
said forming space is cylindrical, has a diameter no less than the diameter of said emitting surface, extends longitudinally from said emitting surface to said exhaust orifice, and is substantially unobstructed by structure, whereby
the ultrasonic waves can form in said forming space without interference by structure.

24. A nozzle for providing a laminar exhaust stream comprising:
a cylindrical plenum chamber formed by an annular longitudinal wall, a first end, and a second end;
an annular passageway laterally circumscribing said plenum chamber, with said wall forming a part of said passageway;
said wall being porous to fluidly communicate said passageway with said plenum chamber;
means for generating ultrasonic energy, with said energy means including a substantially planar emitting surface for emitting the ultrasonic energy;
said first end being comprised of said emitting surface; and
said second end having an annular exhaust orifice.

25. The nozzle recited in claim 24 wherein said exhaust orifice has an annular edge projecting into said plenum chamber.

26. The nozzle recited in claim 25 wherein:
said emitting surface is approximately circular and has a diameter;
said plenum chamber contains a forming space for the formation of ultrasonic waves; and
said forming space is cylindrical, has a diameter no less than the diameter of said emitting surface, extends longitudinally from said emitting surface to said exhaust orifice, and is substantially unobstructed by structure, whereby
the ultrasonic waves can form in said forming space without interference by structure.

27. The nozzle recited in claim 26 wherein:
said annular edge is formed by the intersection of an outer surface of revolution and an inner surface of revolution;
said second end of said plenum chamber includes said outer surface of revolution;
said plenum chamber has an axial centerline that is centrally located in each transverse cross section of said plenum chamber;
said inner and outer surfaces of revolution are symmetrical about said centerline;
an inner angle of at least 30° is included between said centerline and said inner surface of revolution; and
an outer angle no greater than 75° is included between said centerline and said outer surface of revolution.

28. The nozzle recited in claim 25 wherein fluid communication between said passageway and said exhaust orifice is provided solely through said wall.

29. The nozzle recited in claim 25 wherein:
said annular edge is formed by the intersection of an outer surface of revolution and an inner surface of revolution;
said second end of said plenum chamber includes said outer surface of revolution;
said plenum chamber has an axial centerline that is centrally located in each transverse cross section of said plenum chamber;
said inner and outer surfaces of revolution are symmetrical about said centerline;

an inner angle of at least 30° is included between said centerline and said inner surface of revolution; and an outer angle no greater than 75° is included between said centerline and said outer surface of revolution.

30. The nozzle recited in claim 24 wherein:

said plenum chamber has a plenum chamber diameter;

said exhaust orifice has an orifice diameter; and said plenum chamber diameter divided by said orifice diameter has a quotient of at least three.

31. The nozzle recited in claim 30 wherein said exhaust orifice has an annular edge projecting into said plenum chamber.

32. The nozzle recited in claim 31 wherein:

said annular edge is formed by the intersection of an outer surface of revolution and an inner surface of revolution;

said second end of said plenum chamber includes said outer surface of revolution;

said plenum chamber has an axial centerline that is centrally located in each transverse cross section of said plenum chamber;

said inner and outer surfaces of revolution are symmetrical about said centerline;

an inner angle of at least 30° is included between said centerline and said inner surface of revolution; and an outer angle no greater than 75° is included between said centerline and said outer surface of revolution.

33. The nozzle recited in claim 31 wherein:

said emitting surface is approximately circular and has a diameter;

said plenum chamber contains a forming space for the formation of ultrasonic waves; and said forming space is cylindrical, has a diameter no less than the diameter of said emitting surface, extends longitudinally from said emitting surface to said exhaust orifice, and is substantially unobstructed by structure, whereby the ultrasonic waves can form in said forming space without interference by structure.

34. The nozzle recited in claim 30 wherein:

said emitting surface is approximately circular and has a diameter;

said plenum chamber contains a forming space for the formation of ultrasonic waves; and said forming space is cylindrical, has a diameter no less than the diameter of said emitting surface, extends longitudinally from said emitting surface to said exhaust orifice, and is substantially unobstructed by structure, whereby the ultrasonic waves can form in said forming space without interference by structure.

* * * * *